(12) United States Patent
Quinn et al.

(10) Patent No.: US 10,376,170 B2
(45) Date of Patent: Aug. 13, 2019

(54) CATHETER WITH ANNULAR LUMEN TO PROVIDE DISTAL FLUSHING

(71) Applicant: Boston Scientific Scimed Inc., Maple Grove, MN (US)

(72) Inventors: William Quinn, Swampscott, MA (US); Kurt E. Guggenberger, North Andover, MA (US); Ian Collier, Newton, MA (US); Justin Callaway, Goffstown, NH (US); Jeffrey P. Radziunas, Shelton, CT (US); Greg Hires, Shelton, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 242 days.

(21) Appl. No.: 15/232,757

(22) Filed: Aug. 9, 2016

(65) Prior Publication Data

US 2017/0042473 A1 Feb. 16, 2017

Related U.S. Application Data

(60) Provisional application No. 62/203,314, filed on Aug. 10, 2015.

(51) Int. Cl.
*A61B 18/14* (2006.01)
*A61B 5/042* (2006.01)
(Continued)

(52) U.S. Cl.
CPC .......... *A61B 5/0422* (2013.01); *A61B 5/6858* (2013.01); *A61B 18/1492* (2013.01);
(Continued)

(58) Field of Classification Search
CPC . A61B 5/0422; A61B 5/6858; A61B 18/1492; A61N 1/05
See application file for complete search history.

(56) References Cited

U.S. PATENT DOCUMENTS

| 895,370 A | 8/1908 | Hendershot et al. |
| 6,770,071 B2 | 8/2004 | Woloszko et al. |

(Continued)

FOREIGN PATENT DOCUMENTS

| EP | 1350481 B1 | 2/2007 |
| EP | 1707150 B1 | 5/2015 |

(Continued)

*Primary Examiner* — Lee S Cohen
(74) *Attorney, Agent, or Firm* — Faegre Baker Daniels LLP (57) ABSTRACT

A mapping catheter including an elongate catheter body extending from a proximal end to a distal end, a handle connected to the proximal end of the catheter body, an electrode array connected to the distal end, a deployment shaft, and an irrigation system. The catheter body includes at least one lumen. The irrigation system includes a manifold and a thin, polymeric irrigation tube. The manifold is disposed within the handle and is connectable to a source of irrigation fluid. The irrigation tube is connected to the manifold and extends around the deployment shaft from the manifold to the distal end of the catheter through the catheter body lumen. The irrigation tube forms an annular lumen between an inner surface of the irrigation tube and an outer surface of the deployment shaft. The annular lumen is configured to carry irrigation fluid from the manifold to the array.

18 Claims, 4 Drawing Sheets

(51) Int. Cl.
  *A61B 5/00*  (2006.01)
  *A61B 5/06*  (2006.01)
  *A61B 18/00*  (2006.01)
  *A61M 25/01*  (2006.01)

(52) U.S. Cl.
  CPC ..... *A61B 5/062* (2013.01); *A61B 2018/00267* (2013.01); *A61B 2018/00351* (2013.01); *A61B 2018/00577* (2013.01); *A61B 2018/00839* (2013.01); *A61B 2218/002* (2013.01); *A61M 25/0133* (2013.01)

(56) References Cited

U.S. PATENT DOCUMENTS

| | | | |
|---|---|---|---|
| 7,643,886 B2 | 1/2010 | D'Aquanni et al. | |
| 7,892,230 B2 | 2/2011 | Woloszko | |
| 8,447,377 B2 | 5/2013 | Harlev et al. | |
| 8,727,983 B2 | 5/2014 | Kinnison | |
| 8,747,401 B2 | 6/2014 | Gonzalez et al. | |
| 8,790,339 B2 | 7/2014 | Edwards et al. | |
| 8,825,130 B2 | 9/2014 | Just et al. | |
| 8,894,646 B2 | 11/2014 | Edwards et al. | |
| 9,078,667 B2 | 7/2015 | Besser et al. | |
| 9,119,530 B2 | 9/2015 | Abreu | |
| 9,125,666 B2 | 9/2015 | Steinke et al. | |
| 9,168,093 B2 | 10/2015 | Mihalik et al. | |
| 9,186,081 B2 * | 11/2015 | Afonso | A61B 5/0422 |
| 9,186,212 B2 | 11/2015 | Nabutovsky et al. | |
| 9,314,208 B1 | 4/2016 | Altmann et al. | |
| 9,314,299 B2 | 4/2016 | Fang | |
| 9,339,331 B2 | 5/2016 | Tegg et al. | |
| 9,351,736 B2 | 5/2016 | Root et al. | |
| 9,351,787 B2 | 5/2016 | Edwards et al. | |
| 9,402,677 B2 | 8/2016 | Leung et al. | |
| 2003/0171746 A1 * | 9/2003 | Fleischman | A61B 18/1492 606/41 |
| 2017/0035311 A1 * | 2/2017 | Guggenberger | A61B 5/0422 |

FOREIGN PATENT DOCUMENTS

| | | |
|---|---|---|
| EP | 1814482 B1 | 5/2015 |
| EP | 2470099 B1 | 10/2015 |
| EP | 2474340 B1 | 11/2015 |
| EP | 1773227 B1 | 4/2016 |
| EP | 1455669 B1 | 6/2016 |
| EP | 2094333 B1 | 6/2016 |
| EP | 1933756 B1 | 7/2016 |

* cited by examiner

CATHETER WITH ANNULAR LUMEN TO PROVIDE DISTAL FLUSHING

CROSS-REFERENCE TO RELATED APPLICATION

This application claims the benefit of Provisional Application No. 62/203,314, filed Aug. 10, 2015, which is incorporated herein by reference in its entirety.

TECHNICAL FIELD

The present invention relates to medical catheters including a deployable array for use inside a body. More specifically, the invention relates to catheters including an irrigation system for flushing the deployable array inside the body.

BACKGROUND

Cardiac arrhythmias may lead to heart disease and death. Arrhythmias may be treated by medication, implantable devices, or by the ablation of specific heart tissue found to be causing arrhythmia. Ablation may be performed by a number of techniques, including the local application of energy, for example, radio frequency energy, or by the application of cryogenic temperatures to the site of the problem tissue.

The specific heart tissue responsible for arrhythmia in a patient may be identified by moving a mapping catheter having one or more electrodes around the interior of the heart and measuring cardiac signals to sense changes in the electrical fields. A map of the electrical conductivity of the heart may be formed from the measurements to identify abnormalities which may be candidates for ablation. Some mapping catheters are designed such that the electrodes may physically contact the heart wall, including flexible designs that are inserted in a compact form and later deployed into a basket-like array. Such an array is deployed after entrance into the heart, and undeployed upon completion of the mapping and prior to removal from the heart.

During the mapping procedure, it may be beneficial to flush the array with an irrigation fluid, such as a saline solution, to reduce the formation of blood clots on the array. The saline solution may include an anticoagulant, such as heparin, to further reduce clot formation.

SUMMARY

Example 1 is a mapping catheter including an elongate catheter body extending from a proximal end to a distal end, a handle connected to the proximal end of the catheter body, an electrode array connected to the distal end of the catheter body, a deployment shaft extending through the catheter body lumen from the handle to the array, and an irrigation system. The catheter body includes at least one lumen. The array is configurable between an undeployed configuration and a deployed configuration. Linear movement of the deployment shaft changes the configuration of the array. The deployment shaft includes a lumen. The irrigation system includes a manifold and a polymeric irrigation tube. The manifold is disposed within the handle and is connectable to a source of irrigation fluid. The irrigation tube is connected to the manifold and extends around the deployment shaft from the manifold to the distal end of the catheter through the catheter body lumen. The irrigation tube forms an annular lumen between an inner surface of the irrigation tube and an outer surface of the deployment shaft. The annular lumen is configured to carry irrigation fluid from the manifold to the array.

In Example 2, the catheter of Example 1, wherein the manifold includes a manifold body, a nozzle, and an o-ring seal. The manifold body includes a fluid port connectable to the source of irrigation fluid, a fluid chamber fluidly connected to the fluid port, and a deployment shaft port. The nozzle is connected to the manifold body, wherein an interior of the nozzle is in fluid communication with the fluid chamber. The o-ring seal is disposed within the manifold body between the deployment shaft port and the fluid chamber. The deployment shaft extends through the deployment port, the o-ring seal, the fluid chamber, and the interior of the nozzle.

In Example 3, the catheter of Example 2, wherein a proximal end of the irrigation tube is disposed within the interior of the nozzle, and a layer of adhesive is disposed between an outer surface of the irrigation tube and an inner surface of the nozzle to connect the irrigation tube to the manifold.

In Example 4, the catheter of either of Examples 2-3, wherein the manifold body and the nozzle are formed of a transparent polycarbonate.

In Example 5, the catheter of any of Examples 1-4, wherein the deployment shaft is a steel coil reinforced polyimide tube.

In Example 6, the catheter of any of Examples 1-5, wherein a thickness of the irrigation tube is between about 0.013 mm (0.0005 inches) to about 0.13 mm (0.005 inches).

In Example 7, the catheter of Example 6, wherein the thickness of the irrigation tube is between about 0.025 mm (0.001 inches) and 0.10 mm (0.004 inches).

In Example 8, the catheter of any of Examples 1-7, wherein the irrigation tube is formed of a fluoropolymer.

In Example 9, the catheter of Example 8, wherein the fluoropolymer is polytetrafluoroethylene.

In Example 10, the catheter of any of Examples 1-9, wherein the manifold body and the nozzle are formed of a transparent material.

In Example 11, the catheter of any of Examples 1-10, further including an electrical device disposed at a distal end of the array, and at least one conductor extending through the deployment shaft lumen from the handle to the electrical device.

In Example 12, the catheter of Example 11, wherein the electrical device is a magnetic sensor.

In Example 13, the catheter of Example 11, wherein the electrical device is an ablation electrode.

In Example 14, the catheter of any of Examples 1-13, further including a first control wire extending through the catheter lumen from the distal end of the catheter to the handle, and a second control wire extending through the catheter lumen from the distal end of the catheter to the handle, wherein increasing tension on first control wire while decreasing tension on the second control wire deflects the distal end of the catheter in one direction, and decreasing tension on first control wire while increasing tension on the second control wire deflects the distal end of the catheter in another direction to steer the catheter.

In Example 15, the catheter of Example 14, further including a first control wire coil extending around the first control wire from the handle to the distal end of the catheter through the catheter body lumen, and a second control wire coil extending around the second control wire from the handle to the distal end of the catheter.

Example 16 is a mapping catheter including an elongate catheter body extending from a proximal end to a distal end, a handle connected to the proximal end of the catheter body, an electrode array connected to the distal end of the catheter body, a deployment shaft extending through the catheter body lumen from the handle to the array, an electrical device disposed at a distal end of the array, at least one conductor extending through the deployment shaft lumen from the handle to the electrical device, and an irrigation system. The catheter body includes at least one lumen. The array is configurable between an undeployed configuration and a deployed configuration. Linear movement of the deployment shaft changes the configuration of the array. The deployment shaft includes a lumen. The irrigation system includes a manifold disposed within the handle and a polymeric irrigation tube. The manifold is connectable to a source of irrigation fluid. The irrigation tube is connected to the manifold and extending around the deployment shaft from the manifold to the distal end of the catheter through the catheter body lumen. The irrigation tube forms an annular lumen between an inner surface of the irrigation tube and an outer surface of the deployment shaft. The annular lumen is configured to carry irrigation fluid from the manifold to the array.

In Example 17, the catheter of Example 16, wherein the manifold includes a manifold body, a nozzle, and an o-ring seal. The manifold body includes a fluid port connectable to the source of irrigation fluid, a fluid chamber fluidly connected to the fluid port, and a deployment shaft port. The nozzle is connected to the manifold body, wherein an interior of the nozzle is in fluid communication with the fluid chamber. The o-ring seal is disposed within the manifold body between the deployment shaft port and the fluid chamber. The deployment shaft extends through the deployment port, the o-ring seal, the fluid chamber, and the interior of the nozzle.

In Example 18, the catheter of Example 17, wherein a proximal end of the irrigation tube is disposed within the interior of the nozzle, and a layer of adhesive is disposed between an outer surface of the irrigation tube and an inner surface of the nozzle to connect the irrigation tube to the manifold.

In Example 19, the catheter of either of Examples 17 or 18, wherein the manifold body and the nozzle are formed of a transparent polycarbonate.

In Example 20, the catheter of any of Examples 16-19, wherein the deployment shaft is a steel coil reinforced polyimide tube.

In Example 21, the catheter of any of Examples 16-20, wherein a thickness of the irrigation tube is between about 0.013 mm (0.0005 inches) to about 0.13 mm (0.005 inches).

In Example 22, the catheter of any of Examples 16-21, wherein the thickness of the irrigation tube is between about 0.025 mm (0.001 inches) and 0.10 mm (0.004 inches).

In Example 23, the catheter of any of Examples 16-22, wherein the irrigation tube is formed of a fluoropolymer.

In Example 24, the catheter of Example 23, wherein the fluoropolymer is polytetrafluoroethylene.

In Example 25, the catheter of any of Examples 16-24, wherein the electrical device is a magnetic sensor.

In Example 26, the catheter of any of Examples 16-24, wherein the electrical device is an ablation electrode.

In Example 27, the catheter of any of Examples 16-26, further including a first control wire extending through the catheter lumen from the distal end of the catheter to the handle, and a second control wire extending through the catheter lumen from the distal end of the catheter to the handle, wherein increasing tension on first control wire while decreasing tension on the second control wire deflects the distal end of the catheter in one direction, and decreasing tension on first control wire while increasing tension on the second control wire deflects the distal end of the catheter in another direction to steer the catheter.

In Example 28, the catheter of Example 27, further including a first control wire coil extending around the first control wire from the handle to the distal end of the catheter through the catheter body lumen, and a second control wire coil extending around the second control wire from the handle to the distal end of the catheter.

Example 29 is a mapping catheter including an elongate catheter body extending from a proximal end to a distal end, the catheter body including at least one lumen; a handle connected to the proximal end of the catheter body, an electrode array connected to the distal end of the catheter body, a deployment shaft extending through the catheter body lumen from the handle to the array, and an irrigation system. The array is configurable between an undeployed configuration and a deployed configuration. Linear movement of the deployment shaft changes the configuration of the array. The deployment shaft includes a lumen. The irrigation system includes a manifold disposed within the handle and a polymeric irrigation tube. The manifold is connectable to a source of irrigation fluid. The manifold includes a manifold body, a nozzle, and an o-ring seal. The manifold body includes a fluid port connectable to the source of irrigation fluid, a fluid chamber fluidly connected to the fluid port, and a deployment shaft port. The nozzle is connected to the manifold body, wherein an interior of the nozzle is in fluid communication with the fluid chamber. The o-ring seal is disposed within the manifold body between the deployment shaft port and the fluid chamber. The deployment shaft extends through the deployment port, the o-ring seal, the fluid chamber, and the interior of the nozzle. The irrigation tube is connected to the manifold and extends around the deployment shaft from the manifold to the distal end of the catheter through the catheter body lumen. The irrigation tube forms an annular lumen between an inner surface of the irrigation tube and an outer surface of the deployment shaft. The annular lumen is configured to carry irrigation fluid from the manifold to the array.

In Example 30, the catheter of Example 29, wherein a proximal end of the irrigation tube is disposed within the interior of the nozzle, and a layer of adhesive is disposed between an outer surface of the irrigation tube and an inner surface of the nozzle to connect the irrigation tube to the manifold.

In Example 31, the catheter of either of Examples 29 or 30, wherein the manifold body and the nozzle are formed of a transparent material.

In Example 32, the catheter of any of Examples 29-31, further including a magnetic sensor disposed at a distal end of the array, and a plurality of conductors extending through the deployment shaft lumen from the handle to the electrical device.

In Example 33, the catheter of any of Examples 29-32, wherein a thickness of the irrigation tube is between about 0.013 mm (0.0005 inches) to about 0.13 mm (0.005 inches).

In Example 34, the catheter of any of Examples 29-33, wherein the irrigation tube is formed of a fluoropolymer.

In Example 34, the catheter of Example 34, wherein the fluoropolymer is polytetrafluoroethylene.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

Catheters embodying the present invention may be employed in cardiac mapping catheters as described in "CARDIAC MAPPING CATHETER" (U.S. Pat. No. 8,447,377, issued May 21, 2013), hereby incorporated by reference in its entirety. Such catheters typically have several flexible splines forming an array, each spline including a plurality of electrodes. Catheter embodiments of the present invention include an irrigation system that permits flushing of the electrode array with a saline solution. The irrigation system includes a thin, polymeric irrigation tube surrounding a deployment shaft to create an annular lumen for delivery of the saline solution. The annular lumen efficiently uses space within the catheter, freeing up space for the many other components extending down the length of the catheter. The result may be a less invasive, smaller diameter catheter.

Figure 1A:
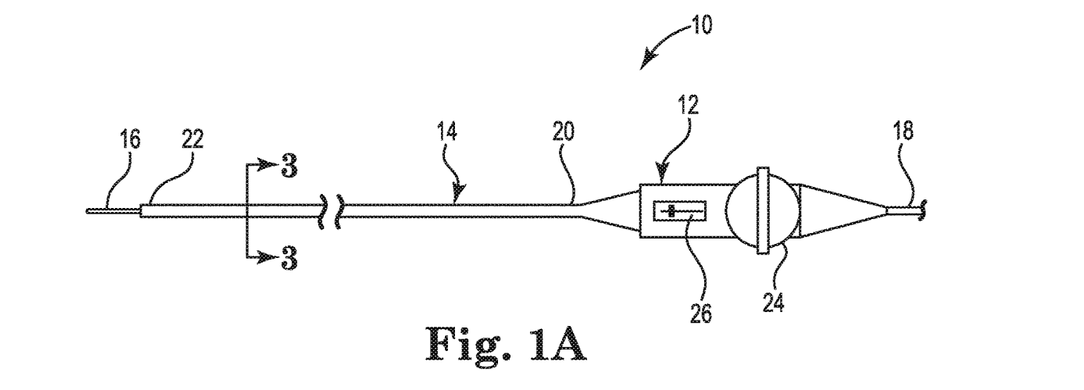
FIGS. 1A-1C are schematic views of a mapping catheter suitable for use with embodiments of the present invention.
Figure 1B:
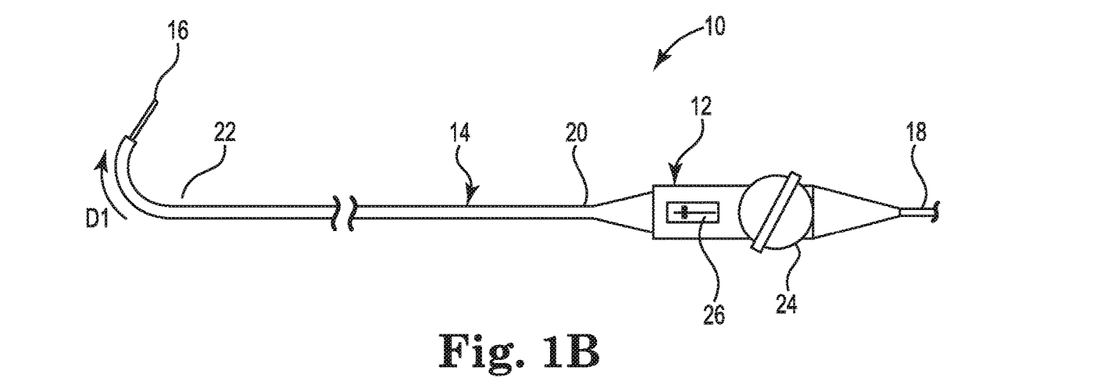
Figure 1C:
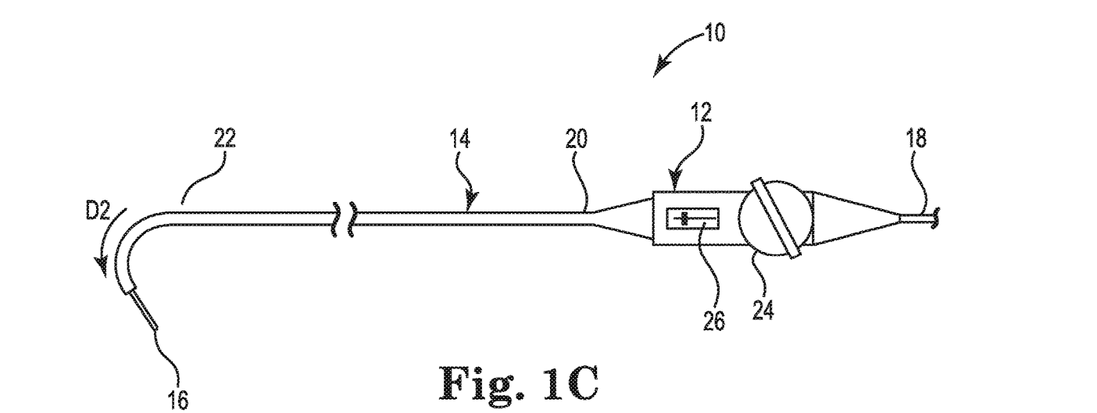

FIGS. 1A-1C provide an illustrative but non-limiting example of a catheter 10 including an embodiment of an irrigation system. As shown in FIGS. 1A-1C, the catheter 10 may include a handle 12, an elongate catheter body 14, an electrode array 16, and an electrical connection 18. The catheter body 14 may extend from a proximal end 20 to a distal end 22. In one embodiment, the catheter body 14 may have an outer diameter of about 8.5 French, although those skilled in the art will recognize that other embodiments may have different outer diameters depending on the particular clinical needs for the catheter 10. The electrode array 16 may project from the distal end 22 of the catheter body 14. In one embodiment, the electrode array 16 includes a plurality of mapping electrodes. In the embodiment illustrated in FIGS. 1A-1C, the electrode array Ser. No. 16 is shown in an undeployed configuration for ease of illustration. The catheter body 14 may be connected at the proximal end 20 to the handle 12. The electrical connection 18 may extend from the handle 12 to a mapping data recording and analysis system (not shown).

The handle 12 may include a steering control 24 and a deployment control 26. The deployment control 26 may include a deployment shaft 28 (shown in FIGS. 2B, 3 and 4) to deploy the electrode array 16, as described below in reference to FIGS. 2A and 2B. The deployment shaft 28 may extend from handle 12 to the electrode array 16 by way of a catheter body lumen 40 (shown in FIG. 3) extending through the catheter body 14 from the proximal end 20 to the distal end 22.

The steering control 24 may control bending of the distal end 22 of the catheter body 14. Bending the distal end 22 provides for flexibility in maneuvering the electrode array 16 within a patient's heart. The catheter 10 may include a first control wire 42 and a second control wire 44 (shown in FIG. 3) extending from the steering control 24 to the distal end 22 by way of the catheter body lumen 40 (shown in FIG. 3) for bending the distal end 22. FIGS. 1A-1C illustrate control of the deflection of the distal end 22 by the steering control 24. FIG. 1A shows the distal end 22 in an undeflected position with the steering control 24 in a corresponding neutral position. FIG. 1B shows the steering control 24 rotated in a direction clockwise from the neutral position to deflect the distal end 22 in a first direction D1 by increasing tension on the first control wire 42 while decreasing tension on the second control wire 44. FIG. 1C shows the steering control 24 rotated in a direction counterclockwise from the neutral position to deflect the distal end 22 in a second direction D2 by decreasing tension on the first control wire 42 while increasing tension on the second control wire 44. As shown in FIGS. 1B and 1C, the second direction D2 is different from the first direction D1. Once the distal end 22 is deflected as desired, a braking knob (not shown) may be rotated to produce a level of friction sufficient to prevent movement of the steering control 24 to maintain the deflection of the distal end 22.

Figure 2A:
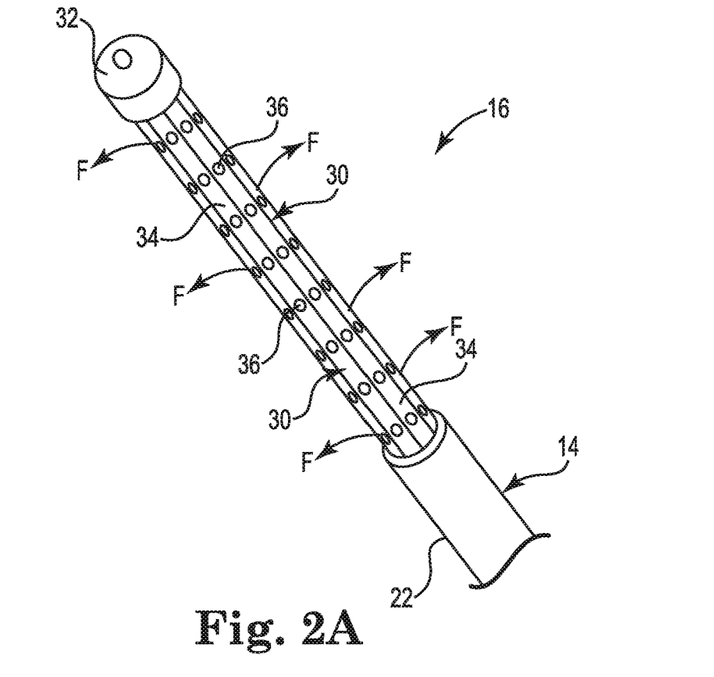
FIGS. 2A-2B are partial perspective views showing a distal end of the mapping catheter of FIGS. 1A-1C.
Figure 2B:
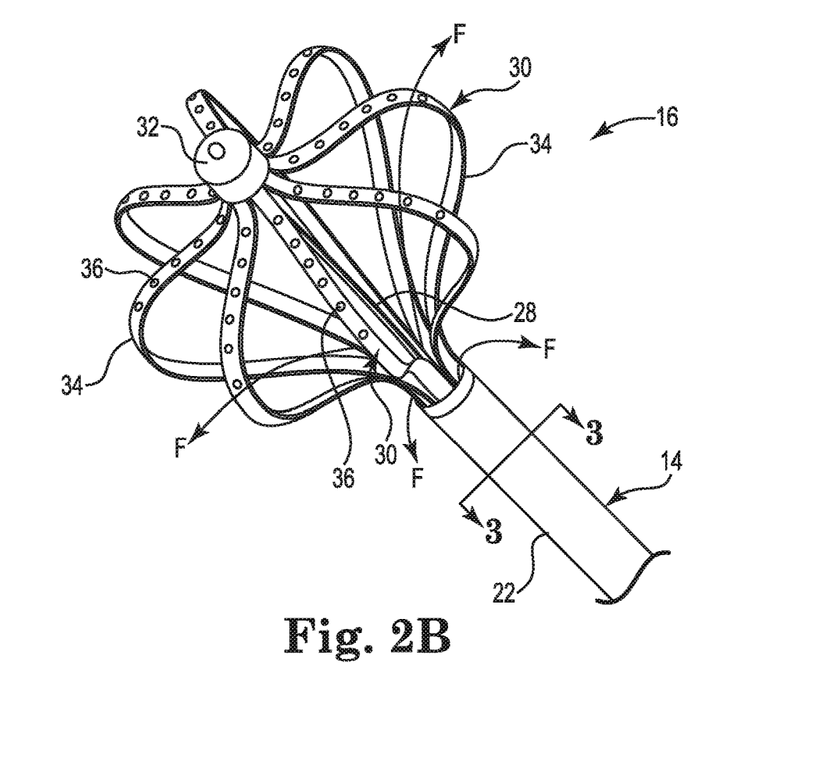

FIGS. 2A and 2B are partial perspective views showing the electrode array 16 and the distal end 22 of the cardiac mapping catheter 10 of FIGS. 1A-1C. FIG. 2A shows the electrode array 16 undeployed in a radially retracted state. FIG. 2B shows the electrode array 16 deployed in a radially extended state. As shown in FIGS. 2A and 2B, the electrode array 16 may include a plurality of splines 30 and an end cap 32. Each of the plurality of splines 30 may extend between the distal end 22 and the end cap 32. Each of the splines 30 may include a flexible polymer substrate 34 and a plurality of electrodes 36. In the exemplary embodiment shown in FIGS. 2A and 2B, there are eight splines 30, each including eight electrodes 36, for a total of sixty-four electrodes 36 in the electrode array 16.

As shown in FIG. 2B, the deployment shaft 28 may extend from the end cap 32 and into the catheter body 14 at the distal end 22. The deployment shaft 28 may be a braided polyimide shaft connecting end cap 32 to the deployment control 26 (see FIG. 3) such that actuation of the deployment control 26 may cause linear movement of the deployment shaft 28 in the proximal direction, and pull the end cap 32 in the proximal direction. Movement of the end cap 32 in the proximal direction may cause the plurality of splines 30 to flex radially outward and deploy the electrode array 16 as shown in FIG. 2B.

In some embodiments, the end cap 32 may include an electrode for cardiac stimulation or tissue ablation. In other embodiments, the end cap 32 may include a magnetic sensor, or have a magnetic sensor coupled thereto, for use in determining the location of the electrode array 16 within the body. In such embodiments, one or more conductors 46 (shown in FIG. 3) may extend from the end cap 32 to at least the handle 12 by way of a deployment shaft lumen 52 (shown in FIG. 3) within the deployment shaft 28 to connect the end cap 32 to the mapping data recording and analysis system.

In use, the cardiac mapping catheter 10 may be inserted into a patient's vasculature with the electrode array 16 in the undeployed, radially retracted state shown in FIG. 2A and steered to the interior of the patient's heart with the steering control 24. Once within the heart, the electrode array 16 may be deployed by deployment control 26 as described above into the radially extended state shown in FIG. 2B to sense the cardiac signals within the heart. The sensed cardiac signals may be transmitted to the mapping data recording and analysis system by way of the set of electrical conductors extending through the catheter body 14 from the electrode array 16 to the handle 12, and the electrical connection 18. Once the cardiac mapping is completed, the electrode array 16 may be undeployed into the radially retracted state and withdrawn from the patient.

Throughout the medical procedure, the electrode array 16 may be flushed with a flow F of irrigation fluid, as shown in both FIGS. 2A and 2B, to reduce the formation of blood clots on the array. The flow F issues from the distal end 22.

Figure 3:
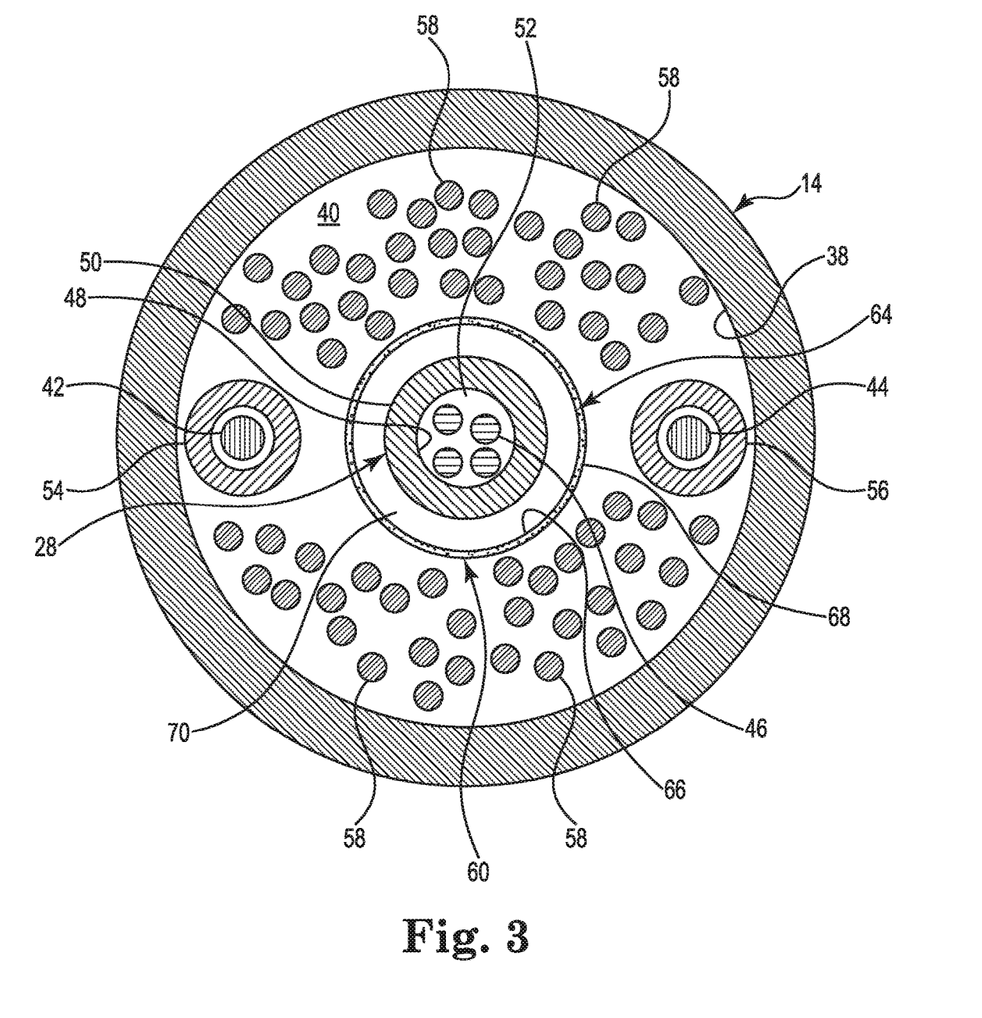
FIG. 3 is a schematic cross-sectional view of the catheter body of the mapping catheter of FIGS. 1A-1C illustrating a portion of an irrigation system embodiment.

FIG. 3 is a schematic cross-sectional view of the catheter body 14. As shown in FIG. 3, the catheter body 14 includes an inner surface 38 defining the catheter body lumen 40. The catheter body lumen 40 contains the deployment shaft 28, the first control wire 42, the second control wire 44, and the at least one conductor 46 as described above. As shown in FIG. 3, the deployment shaft 28 includes an inner surface 48 and an outer surface 50. The inner surface 48 defines the deployment shaft lumen 52. In some embodiments, the magnetic sensor included in or coupled to the end cap 32 may require four conductors 46 extending through the lumen 52, as shown in FIG. 3. In other embodiments, in which the end cap 32 contains an ablation electrode, fewer conductors 46 may be required.

FIG. 3 further shows that the catheter body lumen 40 also contains a first control wire coil 54, a second control wire coil 56, a plurality of signal wires 58, and an irrigation system 60. The first control wire coil 54 and the second control wire coil 56 are tightly wound metal coils extending from the handle 12 to the distal end 22 to contain and provide mechanical support for the first control wire 42 and the second control wire 44, respectively. The plurality of signal wires 58 extend from the electrode array 16 to at least the handle 12 to connect the electrodes 36 to the mapping data recording and analysis system (see FIGS. 1A-2B). In the embodiment described above, the electrode array 16 includes sixty-four electrodes 36. Each of the electrodes 36 requires at least one signal wire 58. Thus, there may be at least sixty-four signal wires 58 extending through the catheter body lumen 40, as shown in FIG. 3. The irrigation system 60 includes a manifold 62 and an irrigation tube 64. The manifold 62 (shown in FIG. 4) may be disposed within the handle 12. The irrigation tube 64 extends through the catheter body lumen 40 from the manifold 62 to the distal end 22. The irrigation tube 64 is a thin, polymeric tube and includes an inner surface 66 and an outer surface 68. The irrigation tube 64 extends around the deployment shaft 28 to form an annular lumen 70. The annular lumen 70 may be configured to carry the flow F of irrigation fluid from the manifold 62 to the electrode array 16 at the distal end 22.

The wall thickness of the irrigation tube 64 may depend on the particular mechanical and operational characteristics required for the irrigation tube 64. In some embodiments, the irrigation tube 64 may have a wall thickness of as little as about 0.013 mm (0.0005 inches), about 0.025 mm (0.001 inches), or about 0.051 mm (0.002 inches), or as great as about 0.076 mm (0.003 inches), about 0.10 mm (0.004 inches), or about 0.13 mm (0.005 inches), or have a wall thickness within any range defined between any pair of the foregoing values. In exemplary embodiments, the irrigation tube 64 may have a wall thickness from about 0.013 mm (0.0005 inches) to about 0.13 mm (0.005 inches), from about 0.025 mm (0.001 inches) to about 0.10 mm (0.004 inches), or from about 0.051 mm (0.002 inches) to about 0.076 mm (0.003 inches).

In some embodiments, the irrigation tube 64 may be formed of a fluoropolymer, for example, polytetrafluoroethylene. In other embodiments, the irrigation tube 64 may be formed of polyethylene, nylon, or a polysiloxane.

As apparent from FIG. 3 and the above description, the catheter body lumen 40 may contain many components, each occupying a portion of the cross-sectional area of the catheter body lumen 40. The annular lumen 70 uses space within the catheter body lumen 40 more efficiently than would, for example, a typical round lumen of comparable cross-sectional area. Additionally, because the wall thickness of the irrigation tube 64 may be very thin, the irrigation tube 64 itself occupies little of the cross-sectional area of the cathode body lumen 40. This efficient use of space frees up space for the many components extending down the length of the catheter. The result may be a less invasive, smaller diameter catheter.

The irrigation tube 64 may also be very flexible, due in part to its wall thickness and/or material selection. This flexibility allows the irrigation tube 64 to conform in response to impingement from some of the many components within the catheter body lumen 40, and not become kinked when bent. Pressure from the flow F of irrigation fluid pushes the irrigation tube 64 open to allow the irrigation fluid to flow.

Figure 4:
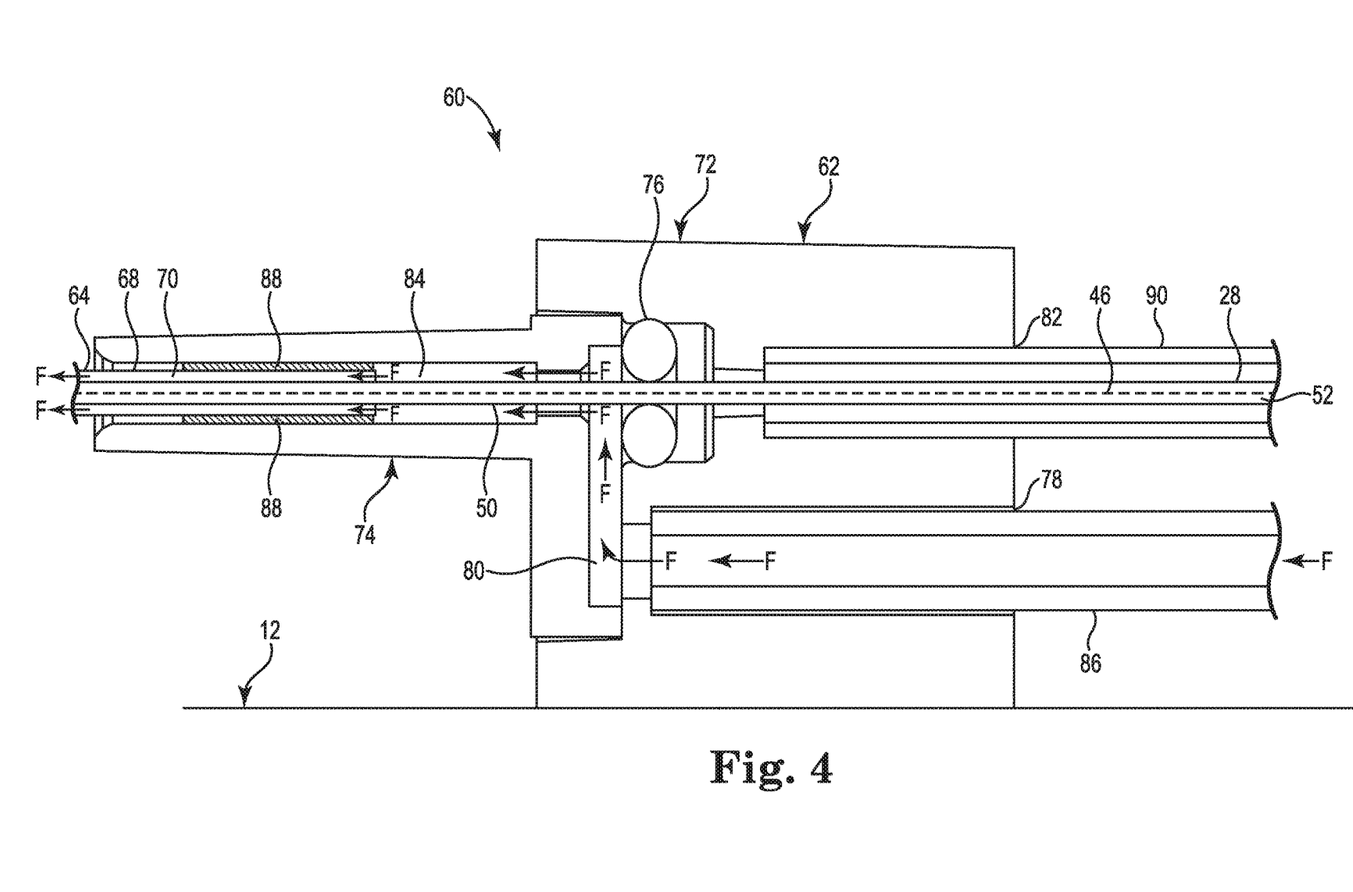
FIG. 4 is a schematic side cross-sectional view of the irrigation system of FIG. 3.

FIG. 4 is a schematic side cross-sectional view of a portion of the irrigation system 60 including the manifold 62. The manifold 62 may be disposed within, and connected, to handle 12. As shown in FIG. 4, the manifold 62 includes a manifold body 72, a nozzle 74, and an o-ring seal 76. The manifold body 72 includes a fluid port 78, a fluid chamber 80, and a deployment shaft port 82. The nozzle 74 includes an inner surface 84. The fluid port 78 may be connectable to a source of irrigation fluid supplied by fluid supply tube 86. The fluid chamber 80 may be fluidly connected to the fluid port 78. The nozzle 74 may be connected to the manifold body 72 such that an interior of the nozzle 74 defined by the inner surface 84 may be in fluid communication with the fluid chamber 80. A proximal end of the irrigation tube 64 may be disposed within the interior of the nozzle 74. A layer of adhesive 88 may be disposed between the outer surface 68 of the irrigation tube 64 and the inner surface 84 to connect the irrigation tube 64 to the manifold 62. The o-ring seal 76 may be disposed within the manifold body 72 between the deployment shaft port 82 and the fluid chamber 80.

The deployment shaft 28 extends from the interior of handle 12, through deployment shaft port 82, the o-ring seal 76, the fluid chamber 80, the interior of the nozzle 74 and the catheter body lumen 40. As shown in FIG. 4, the deployment shaft 28 may be mechanically supported at the deployment shaft port 82 by a rigid tube 90. During the medical procedure, the flow F of irrigation fluid may be from the fluid supply tube 86, through the fluid port 78, and to the fluid chamber 80. From the chamber 80, the irrigation fluid flows around the outer surface 50 of the deployment shaft 28, and into the annular lumen 70. The o-ring seal 80 seals around the deployment shaft 28 to reduce leakage of irrigation fluid from the fluid chamber 80 into the deployment shaft port 82 and into the interior of the handle 12. The o-ring seal 76 permits linear movement of the deployment shaft 28 while maintaining the around the deployment shaft 28.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A mapping catheter comprising:
    an elongate catheter body extending from a proximal end to a distal end, the catheter body including at least one lumen;
    a handle connected to the proximal end of the catheter body;
    an electrode array connected to the distal end of the catheter body, the array configurable between an undeployed configuration and a deployed configuration;
    a deployment shaft extending through the catheter body lumen from the handle to the array, the deployment shaft including a lumen, wherein linear movement of the deployment shaft changes the configuration of the array;
    an electrical device disposed at a distal end of the array;
    at least one conductor extending through the deployment shaft lumen from the handle to the electrical device; and
    an irrigation system including:
        a manifold disposed within the handle, the manifold connectable to a source of irrigation fluid, the manifold including a manifold body, the manifold body including:
            a fluid port connectable to the source of irrigation fluid;
            a fluid chamber fluidly connected to the fluid port; and
            a deployment shaft port;
        a nozzle connected to the manifold body, wherein an interior of the nozzle is in fluid communication with the fluid chamber; and
        an o-ring seal disposed within the manifold body between the deployment shaft port and the fluid chamber, wherein the deployment shaft extends through the deployment port, the o-ring seal, the fluid chamber, and the interior of the nozzle; and
        a polymeric irrigation tube connected to the manifold and extending around the deployment shaft from the manifold to the distal end of the catheter body through the catheter body lumen, wherein the irrigation tube forms an annular lumen between an inner surface of the irrigation tube and an outer surface of the deployment shaft, the annular lumen configured to carry irrigation fluid from the manifold to the array.

2. The catheter of claim 1, wherein a proximal end of the irrigation tube is disposed within the interior of the nozzle, and a layer of adhesive is disposed between an outer surface of the irrigation tube and an inner surface of the nozzle to connect the irrigation tube to the manifold.

3. The catheter of claim 1, wherein the manifold body and the nozzle are formed of a transparent polycarbonate.

4. The catheter of claim 1, wherein the deployment shaft is a steel coil reinforced polyimide tube.

5. The catheter of claim 1, wherein a thickness of the irrigation tube is between about 0.013 mm (0.0005 inches) to about 0.13 mm (0.005 inches).

6. The catheter of claim 5, wherein the thickness of the irrigation tube is between about 0.025 mm (0.001 inches) and 0.10 mm (0.004 inches).

7. The catheter of claim 1, wherein the irrigation tube is formed of a fluoropolymer.

8. The catheter of claim 7, wherein the fluoropolymer is polytetrafluoroethylene.

9. The catheter of claim 1, wherein the electrical device is a magnetic sensor.

10. The catheter of claim 1, wherein the electrical device is an ablation electrode.

11. A mapping catheter comprising:
    an elongate catheter body extending from a proximal end to a distal end, the catheter body including at least one lumen;
    a handle connected to the proximal end of the catheter body;
    an electrode array connected to the distal end of the catheter body, the array configurable between an undeployed configuration and a deployed configuration;
    a deployment shaft extending through the catheter body lumen from the handle to the array, the deployment shaft including a lumen, wherein linear movement of the deployment shaft changes the configuration of the array; and
    an irrigation system including:
        a manifold disposed within the handle, the manifold connectable to a source of irrigation fluid, the manifold including:
            a manifold body including:
                a fluid port connectable to the source of irrigation fluid;
                a fluid chamber fluidly connected to the fluid port; and
                a deployment shaft port;
            a nozzle connected to the manifold body, wherein an interior of the nozzle is in fluid communication with the fluid chamber; and
            an o-ring seal disposed within the manifold body between the deployment shaft port and the fluid chamber, wherein the deployment shaft extends through the deployment port, the o-ring seal, the fluid chamber, and the interior of the nozzle; and
        a polymeric irrigation tube connected to the manifold and extending around the deployment shaft from the manifold to the distal end of the catheter body through the catheter body lumen, wherein the irrigation tube forms an annular lumen between an inner surface of the irrigation tube and an outer surface of the deployment shaft, the annular lumen configured to carry irrigation fluid from the manifold to the array.

12. The catheter of claim 11, wherein a proximal end of the irrigation tube is disposed within the interior of the nozzle, and a layer of adhesive is disposed between an outer surface of the irrigation tube and an inner surface of the nozzle to connect the irrigation tube to the manifold.

13. The catheter of claim 11, wherein the manifold body and the nozzle are formed of a transparent material.

14. The catheter of claim 11, further including:
a magnetic sensor disposed at a distal end of the array; and
a plurality of conductors extending through the deployment shaft lumen from the handle to the magnetic sensor.

15. The catheter of claim 11, wherein a thickness of the irrigation tube is between about 0.013 mm (0.0005 inches) to about 0.13 mm (0.005 inches).

16. The catheter of claim 11, wherein the irrigation tube is formed of a fluoropolymer.

17. The catheter of claim 16, wherein the fluoropolymer is polytetrafluoroethylene.

18. A mapping catheter comprising:
an elongate catheter body extending from a proximal end to a distal end, the catheter body including at least one lumen;
a handle connected to the proximal end of the catheter body;
an electrode array connected to the distal end of the catheter body, the array configurable between an undeployed configuration and a deployed configuration;
a deployment shaft extending through the catheter body lumen from the handle to the array, the deployment shaft including a lumen, wherein linear movement of the deployment shaft changes the configuration of the array;
an electrical device disposed at a distal end of the array;
at least one conductor extending through the deployment shaft lumen from the handle to the electrical device; and
an irrigation system including:
   a manifold disposed within the handle, the manifold connectable to a source of irrigation fluid;
   a polymeric irrigation tube connected to the manifold and extending around the deployment shaft from the manifold to the distal end of the catheter body through the catheter body lumen, wherein the irrigation tube forms an annular lumen between an inner surface of the irrigation tube and an outer surface of the deployment shaft, the annular lumen configured to carry irrigation fluid from the manifold to the array;
a first control wire extending through the catheter body lumen from the distal end of the catheter body to the handle;
a second control wire extending through the catheter body lumen from the distal end of the catheter body to the handle, wherein increasing tension on first control wire while decreasing tension on the second control wire deflects the distal end of the catheter body in one direction, and decreasing tension on first control wire while increasing tension on the second control wire deflects the distal end of the catheter body in another direction to steer the catheter;
a first control wire coil extending around the first control wire from the handle to the distal end of the catheter body through the catheter body lumen; and
a second control wire coil extending around the second control wire from the handle to the distal end of the catheter body.

* * * * *